United States Patent
Cook et al.

(10) Patent No.: US 7,146,861 B1
(45) Date of Patent: Dec. 12, 2006

(54) DISPOSABLE AND TRIMMABLE WIRELESS PRESSURE SENSOR

(75) Inventors: James D. Cook, Freeport, IL (US); James ZT Liu, Hudson, NH (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/253,530

(22) Filed: Oct. 18, 2005

(51) Int. Cl.
*G01L 9/12* (2006.01)

(52) U.S. Cl. ............. 73/718; 73/715; 73/716; 73/753

(58) Field of Classification Search ........... 73/700–756
See application file for complete search history.

(56) References Cited

U.S. PATENT DOCUMENTS

| | | | |
|---|---|---|---|
| 5,155,708 A | 10/1992 | Bedi et al. | 367/152 |
| 5,675,314 A | 10/1997 | Chaklader | 340/443 |
| 5,821,425 A | 10/1998 | Mariani et al. | 73/703 |
| 6,055,855 A | 5/2000 | Straub | 73/146.8 |
| 6,314,791 B1 | 11/2001 | Rapp et al. | 73/24.06 |
| 6,517,481 B1 | 2/2003 | Hoek et al. | 600/300 |
| 6,568,271 B1 | 5/2003 | Shah et al. | 73/599 |
| 6,640,613 B1 | 11/2003 | Rapp et al. | 73/24.01 |
| 7,059,195 B1 * | 6/2006 | Liu et al. | 73/753 |
| 2002/0113521 A1 | 8/2002 | Rapp et al. | 310/313 R |
| 2003/0076743 A1 | 4/2003 | Thompson et al. | 367/140 |
| 2003/0139677 A1 | 7/2003 | Fonseca et al. | 600/508 |
| 2003/0196477 A1 | 10/2003 | Auner et al. | 73/24.06 |
| 2004/0242956 A1 * | 12/2004 | Scorvo | 600/30 |

OTHER PUBLICATIONS

D. Kim, B. Kim, H. Kang, B. Ju, *Development of a Piezoelectric Polymer-based Sensorized Microgripper for Microassembly and Micromanipulation*, 2003 IEEE/RSJ Intl. Conference on Intelligent Robots and Systems.

T.R. Hay, J.L. Rose, *Flexible PVDF Comb Transducers for Excitation of Axisymmetirc Guided Waves in Pipe*, Sensors and Actuators A 100 (2002) pp. 18-23.

R.S.C. Monkhouse, P.W. Wilcox, M.J.S. Lowe, R.P. Dalton, P. Cawley, *The Rapid Monitoring of Structures Using Interdigital Lamb Wave Transducers*, Smart Mater. Struct. 9 (2000) pp. 304-309.

J. Huang, *Overview of β-poly (vinylidiene fluoride) and Its Use as a Piezoelectric Polymer*, Mar. 13, 1998.

Y.R. Roh, V.V. Varadan, V.K. Varadan, *Optimal Design of Immersed SAW Devices for High- and Low-Frequency Sensor Applications* Smart Mater. Struct. 5 (1996) pp. 369-378.

I. Lee, H.J. Sung, *Development of an Array of Pressure Sensors with PVDF Film*, Experiments in Fluids 26 (1999) pp. 27-35.

B.R. Patnaik, G.R. Heppler, W.J. Wilson, *Sensor Effectiveness Coefficients for Piezoelectric Materials*, American Control Conference Jun. 1995.

* cited by examiner

*Primary Examiner*—Edward Lefkowitz
*Assistant Examiner*—Jermaine Jenkins
(74) *Attorney, Agent, or Firm*—Kermit D. Lopez; Luis M. Ortiz

(57) ABSTRACT

A disposable pressure sensor includes a substrate and a pressure diaphragm formed upon the substrate. A sensor coil can be provided, comprising a capacitor and an inductor formed on the substrate and surrounded by the pressure diaphragm. The ferrite core is located proximate to the sensor coil, such that when the pressure diaphragm is exposed to a pressure, the diaphragm moves close to the inductor or the capacitor, thereby resulting in a change in the capacitor or the inductor and an indication of pressure. The capacitor can be implanted as an adjustable, trimmable or variable capacitor. The inductor may also be provided as an adjustable or variable inductor and can include the use of a variable capacitor and a PVDF based piezoelectric transducer. When the PVDF layer is under pressure, it can generate an electric field across the interdigital transducer and transmit a signal thereof through an antenna.

20 Claims, 9 Drawing Sheets

DISPOSABLE AND TRIMMABLE WIRELESS PRESSURE SENSOR

TECHNICAL FIELD

Embodiments are generally related to sensing devices and applications. Embodiments are also related to pressure sensor devices, systems and methods thereof. Embodiments are additionally related to low cost disposable sensing devices.

BACKGROUND OF THE INVENTION

A variety of sensors can be utilized to detect conditions, such as pressure and temperature. The ability to detect pressure and/or temperature is an advantage to any device exposed to variable pressure conditions, which can be severely affected by these conditions. An example of such a device is a catheter or a cartridge for hemodialysis machine, which of course, can experience variations in both temperature and pressure. Many different techniques have been proposed for sensing the pressure and/or temperature in catheters and cartridges, and for delivering this information to an operator so that he or she is aware of pressure and temperature conditions associated with a catheter or a cartridge and any fluid, such as blood flowing therein.

One type of sensor that has found wide use in pressure and temperature sensing applications is the Surface Acoustic Wave (SAW) sensor, which can be composed of a sense element on a base and pressure transducer sensor diaphragm that is part of the cover. For a SAW sensor to function properly, the sensor diaphragm should generally be located in intimate contact with the sense element at all pressure levels and temperatures.

One of the problems with current SAW sensor designs, particularly those designs adapted to lower pressure range applications, is the inability of conventional SAW sensing systems to meet the demand in low pressure applications. (e.g., 0 to 500 mmHg), while doing so in an efficient and low cost manner. Such systems are inherently expensive, awkward, and often are not reliable in accurately sensing air pressure and temperature. There is a continuing need to lower the cost of sensor designs utilized in pressure and/or temperature sensing applications, particularly wireless pressure sensors.

A number of conventional passive wireless technologies have been utilized in commercial and industrial applications. For example, an LC resonator (tank) sensor has the potential of being utilized as a low cost sensor with a low interrogation cost, but provides a relatively poor sensor performance. An LC tank with regulated power, an associated ASIC and so forth has also been implemented, such a device may be good for multiple sensing applications, but such a configuration presents a high sensor cost and a large area coil.

PVDF acoustic wave sensors are also known and are based on low cost materials such as polymer along with flexible components thereof, but PVDF acoustic wave sensors are typically both piezo-electric and pyro-electric (i.e., highly temperature dependent), and cannot be exposed to temperatures greater than 120° C. Additionally the dimensions for a PVDF sensor are frequency dependent, such that the higher frequencies increase the associated costs to the sensor. Another example of a conventional sensor is the magneto elastic sensor, which is based on a low cost material, but such a sensor has difficulties in overcoming ambient RF effects, while also possessing long term stability issues associated with permanent magnetic materials, temperature variation and hysteresis problems.

A further example of a passive sensor is a quartz SAW sensor, which is generally accurate but results in a high sensor cost (i.e., material and etching) and trimming thereof lowers the Q value, and hence the performance of the device. Additionally the interrogation electronics (IE) for such a device can be expensive. A PZT SAW sensing device presents an alternative. The PZT material possesses a high coupling coefficient, which makes it possible working in low pressure range without an etched diaphragm. But it is difficult to control PZT chemistry (e.g., grain size, orientation, residual stress, control of nucleation at the at the electrode/PZT interface, Zr/Ti ratio control). PZT SAW sensor devices are also plagued with issues related to electrode materials migration, another drawback to the use of such a device.

A further example of a conventional sensor is the LiNbO3 SAW sensor, which also possesses high coupling coefficient/sensitivity. Such a sensor can be utilized in low pressure measurement without using a costly etching step. The LiNbO3 SAW sensor possesses a lower cost structure than the Quartz SAW sensor, but remains too high for cost-effective applications, particularly when considering its associated sensor packaging and interrogation electronics (IE) costs. Optical sensors represent additional types of conventional sensing applications and utilize optical fibers positioned in front of a flexible reflecting diaphragm. The intensity of the reflected light is related to the pressure induced deflections of the diaphragm. The relative position needs reference sensor, and therefore the alignment is difficult to control in sensing applications. Another drawback to optical sensors is that such devices are susceptible to environmental interference.

To lower the cost and raise efficiency, few components, less expensive materials and fewer manufacturing-processing steps are necessary. In order to achieve these goals, it is believed that a disposable LC tank pressure sensor should be implemented, along with reusable wireless interrogations. To date, such components have not been adequately achieved.

One area where the ability to detect pressure and/or temperature is critically important is in medical applications. Pressure in and out during a dialysis routine, for example, can be measured utilizing several techniques. Perhaps the most common methodology for such pressure measurement involves the use of a pressure sensor, which may be molded inside one wall of the conduit to the fluid pressure within the conduit. Inside the gauge, a needle is deflected over a scale in proportion to the pressure within the conduit. In some instances, the standard pressure gauge may be replaced with a transducer which converts pressure into an electrical signal which is then monitored. One important medical application for a pressure sensor involves detecting a patient's blood pressure, and/or intracranial pressure.

One typical method of monitoring blood pressure is to measure the fluid pressure within an intravenous tube which is hydraulically coupled to the patient's vein. A catheter is inserted into the patient's vein and a plastic tube or conduit coupled to the catheter. A saline solution can be drip-fed through the plastic tubing or conduit to maintain a pressure balance against the pressure within the patient's vein. The saline fluid acts as a hydraulic fluid to cause the pressure within the plastic tubing to correspond to the pressure within the patient's vein. Hence, by measuring the fluid pressure within the tubing, the patient's blood pressure will be known.

Conventional pressure sensors are expensive to implement in medical applications, rendering their wide-spread use limited, particularly in medical applications. It is therefore believed that a solution to such problems involves a disposable low cost sensor packaging system, particularly one which is suited to medical applications.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for improved sensing devices and applications It is another aspect of the present invention to provide for improved pressure sensor devices, systems and methods thereof.

It is a further aspect of the present invention to provide for an improved disposable pressure sensor.

It is an additional aspect of the present invention to provide for a pressure sensor, which can be utilized in medical applications.

The aforementioned aspects of the invention and other objectives and advantages can now be achieved as described herein. Disposable LC wireless pressure sensor systems and methods are disclosed. A substrate can be provided. The substrate can be, for example, plastic, PCB or other low cost materials. In the variable capacitance design, a capacitor electrode and a planar inductor can be printed on the substrate to form a pressure sensor thereof. Another capacitor electrode can be located on the pressure diaphragm. In a variable inductance design, the inductor can be configured to comprise a planar inductor on the substrate and a ferromagnetic pressure diaphragm, such that when the diaphragm is exposed to a pressure, the diaphragm moves close to the planar inductor, thereby resulting in an increase in the inductance and a decrease in the resonant frequency of the LC tank resonant circuit associated with the capacitor and the inductor and any associated circuitry.

Such increase and/or decrease data are detectable by external interrogation. The diaphragm can be configured from a ferromagnetic material, such as, for example, $Fe_3O_4$, alloys containing iron, nickel or cobalt, ferrite lamination, and the like. The diaphragm can also be configured as a bossed or corrugated structure. Interrogation electronics can be associated with the pressure sensor, including the inductor and/or the capacitor, in order to detect the capacitance or inductance variation and changes in the resonant frequency. Calibration can be accomplished utilizing, for example, a laser trimming mechanism for laser trimming the capacitor and/or inductor.

In a preferred embodiment, a disposable pressure sensor can be configured, which includes a substrate and a pressure diaphragm formed upon the substrate. A sensor coil can be provided, comprising a capacitor and an inductor formed on the substrate and surrounded by the pressure diaphragm. A ferrite core is also provided, which is surrounded by the pressure diaphragm. The ferrite core is located proximate to the sensor coil, such that when the pressure diaphragm is exposed to a pressure, the diaphragm moves close to the inductor or the capacitor, thereby resulting in a change in the capacitor or the inductor and an indication of pressure. The capacitor can be implanted as an adjustable, trimmable or variable capacitor. The inductor may also be provided as an adjustable or variable inductor.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
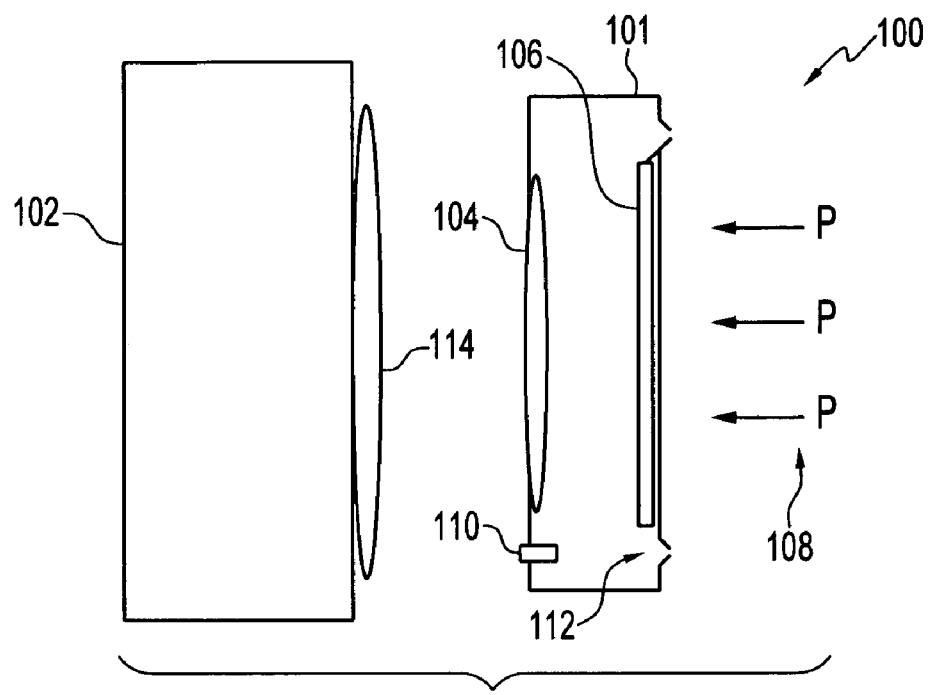
FIG. 1 illustrates a block diagram of a pressure sensor system, which can be implemented in accordance with one embodiment.

FIG. 1 illustrates a block diagram of a pressure sensor system, which can be implemented in accordance with a preferred embodiment. A substrate 101 can be provided upon which a capacitor 110 and an inductor 104 are fixed to the substrate 101 to form a pressure sensor thereof. The inductor 104 can be configured to comprise a planar inductor surface and one ferromagnetic pressure diaphragms 112, such that when the diaphragm 112 is exposed to a pressure as indicated by arrows 108, the diaphragm 112 moves close to the inductor surface, thereby resulting in an increase in the inductance and a decrease in the resonant frequency of the LC tank resonant circuit associated with the capacitor 110 and the inductor 104 and any associated circuitry thereof. Such increases and/or decrease are detectable by external interrogation.

The diaphragm 112 can be configured from a ferromagnetic material 106, such as, for example, $Fe_3O_4$, alloys containing iron, nickel or cobalt, ferrite lamination, and the like. The diaphragm 112 can also be configured as a bossed or a corrugated structure. Interrogation electronics 102 can additionally be associated with the pressure sensor, including the planar inductor 114 (as antenna) and other associated electronics in order to detect the inductance variation and/or changes in the resonant frequency. Calibration can be accomplished utilizing, for example, a laser trimming mechanism (not shown in FIG. 1) for laser trimming the capacitor and/or inductor.

Thus, in the variable inductance configuration, a fixed capacitor 110 and a fixed inductor 104 can be implemented, along with a movable diaphragm 112. The ferromagnetic materials 106 are located on the outside surface of the diaphragm 112. When the diaphragm 112 is under pressure, as indicated by arrows 108, the diaphragm 112 moves (i.e., together with ferromagnetic materials 106) close to inductor 104, so that the inductance thereof increases and any resonant frequency associated with the circuitry thereof decreases. Such a frequency change can be detected utilizing interrogation electronics 102.

Figure 2:
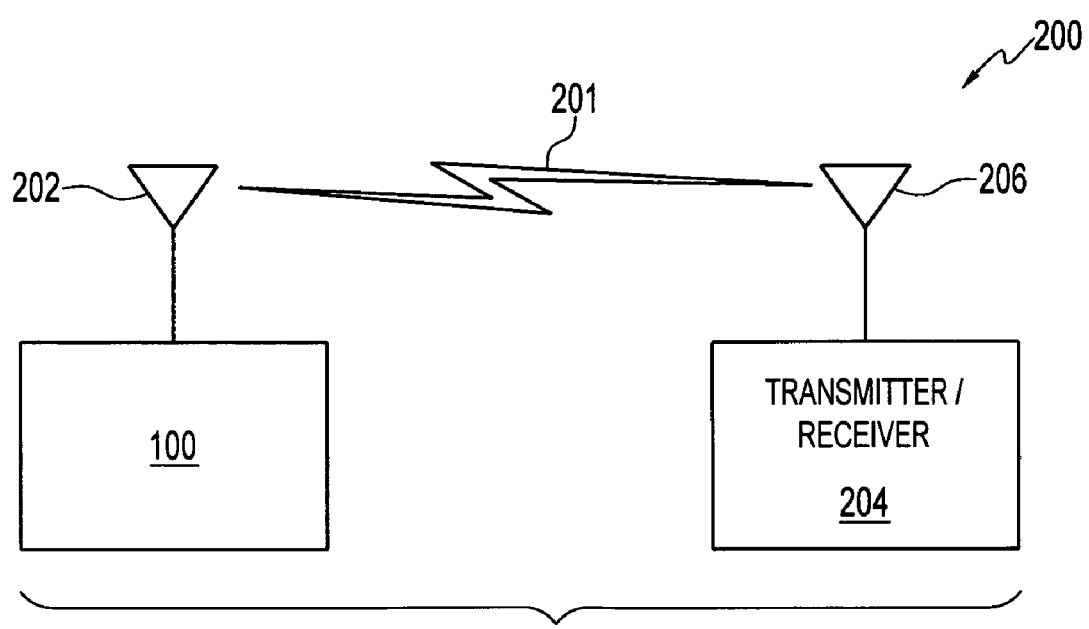
FIG. 2 illustrates a schematic diagram of a system, which can be implemented in accordance with one embodiment.

FIG. 2 illustrates a schematic diagram of a system 200, which can be implemented in accordance with one embodiment. Note that in FIGS. 1–2, identical or similar parts or components are generally indicated by identical reference numerals. Thus, system 100 depicted in FIG. 2 is also illustrated in FIG. 1 in association with an antenna 202 and a transmitter/receiver unit 204, which also includes an antenna 206. System 202 can thus transmit pressure data from antenna 202 to antenna 206. System 200 represents one possible wireless embodiment. Wireless communications between system 100 and transmitter/receiver unit 204 is generally indicated in FIG. 2 by arrow 201.

Figure 3:
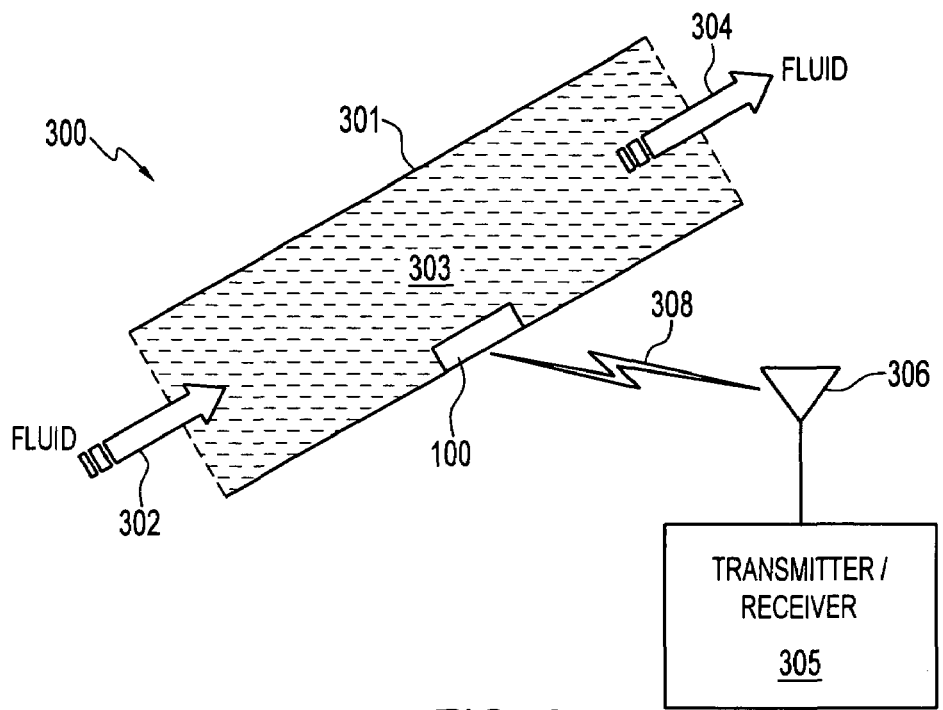
FIG. 3 illustrates a schematic diagram of a medical pressure sensing system, which can be implemented in accordance with another embodiment.

FIG. 3 illustrates a schematic diagram of a medical pressure sensing system 300, which can be implemented in accordance with an alternative embodiment. Note that in FIGS. 1–3, identical or similar parts or components are generally indicated by identical reference numerals. Thus, sensor or system 100 of FIG. 1 is also depicted in FIG. 3 at a location relative to a conduit 301, which can be implemented as, for example, a catheter through which fluid 303 flows, as indicated by arrows 302 and 304. Fluid 303 can be, for example, blood. System or sensor 100 can therefore transmit and receive data to and from a transmitter/receiver 304, which includes an antenna 306. The wireless transmission of such data is indicated in FIG. 3 by arrows 308. System 300 can therefore be utilized for measuring bodily fluid pressure within conduit 301.

Figure 4:
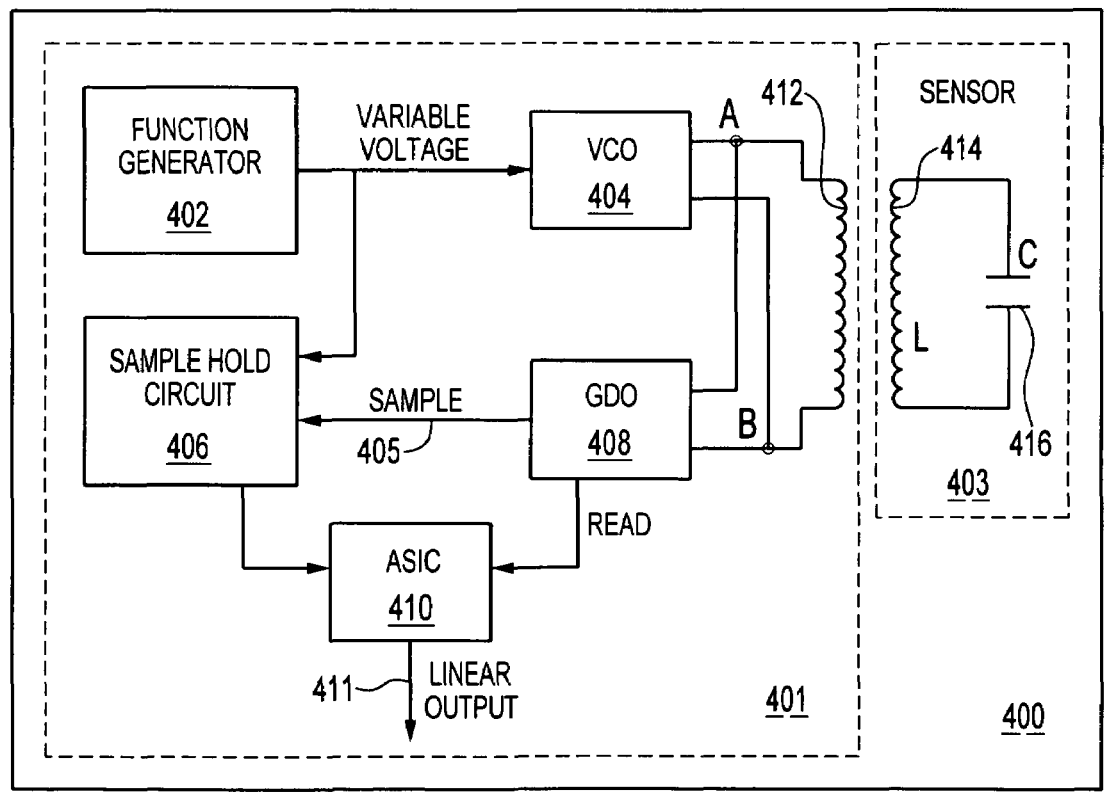
FIG. 4 illustrates a schematic diagram of a sensor system, including associated interrogation electronics, which can be implemented in accordance with an alternative embodiment.

FIG. 4 illustrates a schematic diagram of a sensor system 400, including associated interrogation electronics, which can be implemented in accordance with an alternative embodiment. System 400 generally includes a function generator 402 which provides a variable voltage to an oscillator, VCO 404 and a sample hold circuit 406. The function generator 402 can be configured as an oscillator circuit with an integrator thereof.

Output from sample hold circuit 406 can be provided to an ASIC 410. Output from VCO 404 is generally provided at node A and node B. The interrogation antenna can be, for example, an inductor or coil 412, and is also generally connected to node A and node B and is located adjacent to an inductor or coil 414, which lies in parallel with a capacitor 416. Coil 414 and capacitor 416 together can form a sensor circuit. A Grid Dip Oscillator (GDO) 408 can provide sample data to sample hold circuit 406 and can additionally provide read data to ASIC 410, which in turn provides a linear output signal as indicated by arrow 411.

Two circuits 401 and 403 are therefore effectively coupled to one another through inductive coupling via the configuration of system 400. The first circuit 401 generally provides the interrogation electronic (IE) and is generally composed of function generator 402, a voltage controlled oscillator (i.e., VCO 404), sample hold circuit 406, GDO 408, ASIC 410 and an interrogation inductor or coil 412. The second circuit 403, which functions as a sensor or forms part of a sensor, can be composed of inductor or coil 414 in parallel with capacitor 416.

Inductor or coil 412 functions generally as a probe coil. Thus, when the probe coil 412 is close to the coil 414 of the sensor circuit 403, the two circuits 401 and 403 are effectively coupled through inductive coupling. As the frequency of the oscillator (VCO) 404 is swept, oscillations induced in the sensor circuit 403 will be of very low amplitude until the test oscillator reaches the resonant frequency of the sensor tuned circuit, at which point they will "peak" or increase sharply in amplitude. A high circulating current is thus developed in the sensor circuit 403, which is reflected back into the GDO 408 as high impedance, tending to reduce the level of oscillation, or showing a "dip" in oscillation.

By measuring the "dip," the resonant frequency of the sensor and therefore the displacement (or pressure) of the variable elements coil 414, 416 (L, C or L&C) may be determined. FIG. 4 therefore illustrates a block diagram of the entire sensor system 400. In general, the function generator 402 oscillates at a relatively low frequency with a ramp or triangular waveform and causes VCO 404 to sweep its output between a nominal frequency range. The output of the VCO 404 is directed to probe coil 412, which is inductively coupled to the LC tank sensor circuit 403 formed by inductor or coil 414 and capacitor 416. A "dip" in the probe circuit 401 power due to a resonance condition between the LC sensor circuit 403 and the probe coil 412 can be detected by the GDO circuit 408.

Note that the sample hold circuit 406 generally possesses an input provided by the voltage output of function generator 402. Sample hold circuit 406 also provides an output voltage that can be held at the constant value until another pulse from GDO 408 and comparator is applied to the "sample" input of sample hold circuit 406 as indicated by arrow 405. The output of the sample hold circuit 406 can be directed into a linearization circuit, i.e., ASIC 410.

The output of the ASIC 410 as indicated by arrow 411 can be directed into a voltmeter or an appropriate customer input circuit. Additionally, the function generator 402 can oscillate at a relatively low frequency (e.g., 10 Hz to 100 Hz) with a ramp or triangular waveform that causes the voltage-controlled oscillator VCO 404 to sweep its output between a desired range (e.g. 10 MHz+/−1 MHz).

The interrogation electronics depicted in system 400 are generally associated with inductor 414 and capacitor 416.

Note that capacitor 110 depicted in FIG. 1 is analogous to capacitor 416 illustrated in FIG. 4. Similarly, inductor 104 depicted in FIG. 1 is analogous to inductor or coil 414 illustrated in FIG. 4. Likewise, the interrogation electronics 102 illustrated in FIG. 1 is analogous to the interrogation electronics of circuit 401 depicted in FIG. 1. Thus, system 400 can be implemented in the context of the configuration depicted in FIGS. 1–3 herein.

The determination of pressure applied to sensor circuit 403 is generally independent of the amplitude of the response, and may dependent only on the frequency of resonant oscillation, which is inherently a digital measurement. Digital measurement can be configured with greater accuracy through the utilization of an analog quantity, because measurement drift and gain instability do not affect the digital measurement. The accuracy of a frequency count is dependent solely on the stability of the time base. With a crystal oscillator time base, for example, stabilities of 1 PPM are commonplace. The accuracy with which the resonant frequency of the sensor may be determined is limited only by the ability to resolve the "peak" or "dip" of the response. This is a function of the sharpness of the response peak of the transducer resonant circuit, which can be determined by a circuit "Q" or quality factor. Because a circuit "Q" is simply the ration of the circuit reactance to circuit resistance, the transducers should be designed to possess the highest possible inductance or capacitance and the lowest possible resistance to ensure a high "Q".

Figure 5:
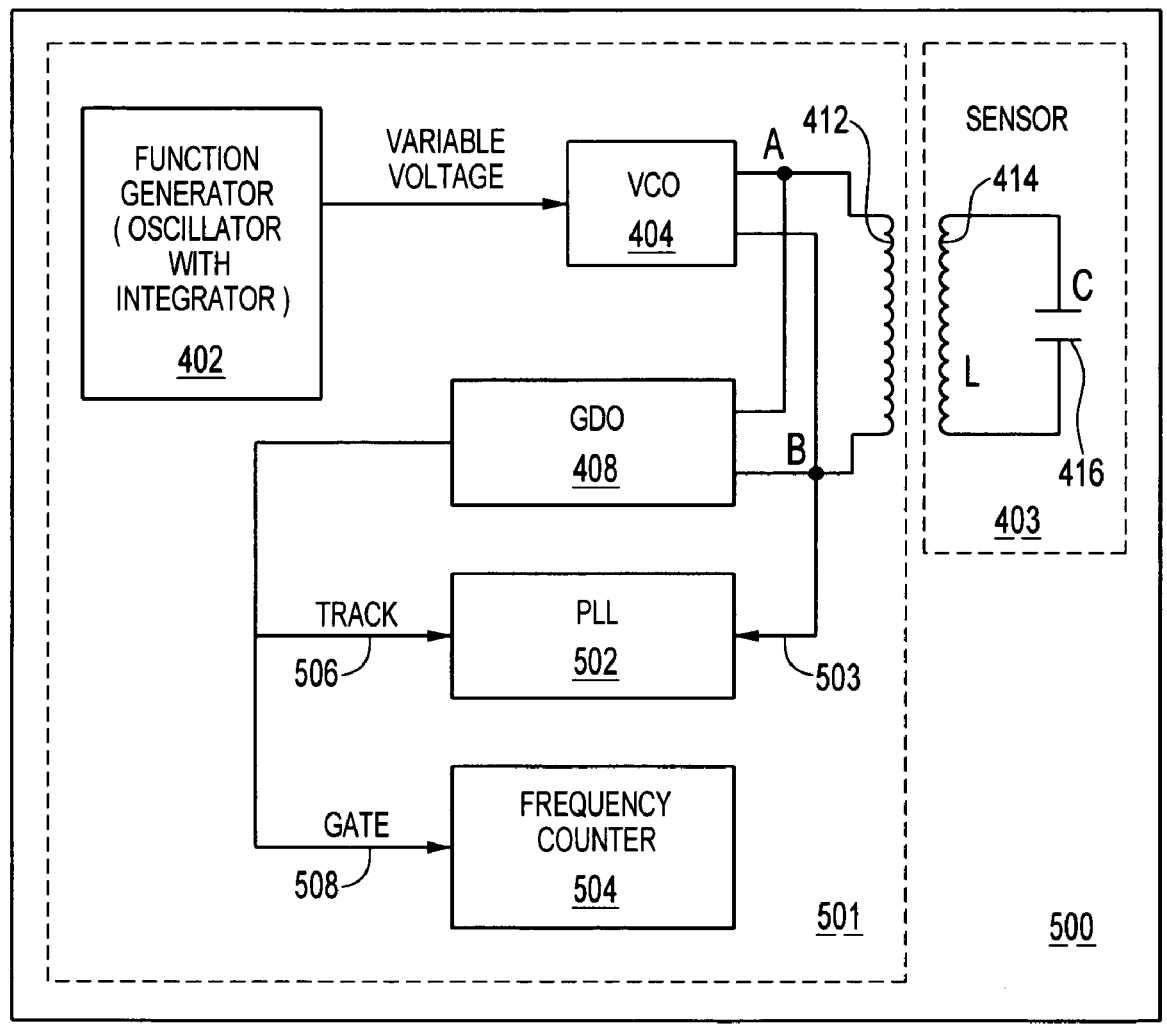
FIG. 5 illustrates a schematic diagram of a system, which can be implemented in accordance with an alternative embodiment.

FIG. 5 illustrates a schematic diagram of a system 500, which can be implemented in accordance with an alternative embodiment. Note that in FIGS. 1–5, identical or similar elements and components are generally indicated by identical reference numerals. Thus, in system 500, function generator 402 can output a ramp or triangular waveform at a relative low frequency (e.g., between 100 and 1000 Hz). The voltage output of function generator 402 can be directed into voltage controlled oscillator (VCO) 404, whose output is a radiofrequency sinusoidal waveform at a frequency, which is proportional to the input voltage.

Thus, the output of VCO 404 can be implemented as a swept radio frequency signal sweeping between a desired range (e.g., 10 MHz+/−1 MHz). The output of VCO 404 drives the probe coil 412, which can be brought into proximity to the LC sensor circuit formed by inductor 414 and capacitor 416. A portion of the output of VCO 404 can be directed into a tracking oscillator 408 and/or a phase-locked loop (PLL) circuit 502, the output of which normally tracks and remains synchronized with the input frequency from the VCO 404. Signal proportional to the instantaneous power driving probe coil 412 can be directed into GDO 408 in order to generate an output pulse at the minimum point of the "dip" response as indicated in FIG. 5 as the VCO frequency is swept. Note that in configuration of system 500, node B can be tied to PLL 502, thereby providing an input voltage to PLL 502 as indicated by arrow 503.

A number of methods can be utilized for detecting the "dip," such as a differentiating circuit followed by a zero-crossing detector. The pulse output of the GDO 408 is present only when a dip has been detected, and then only at the minimum point of the dip where the derivative is zero. This output can be directed to the tracking oscillator/PLL 502 in order to "freeze" its frequency of oscillation at the input frequency at the instant where the "dip" was detected. The same signal can be utilized to gate a frequency counter 504, which can read the output frequency of the tracking oscillator/PLL 502 and displays the resultant count.

System 500 can be implemented in the context of a medical application, such as, for example, a dialysis machine. A dialysis machine typically includes a dialysis cartridge. When the dialysis cartridge is away from the dialysis machine, the probe coil 412 is distant from a resonant sensor and no dip is detected by the GDO 408 as the VCO 404 is swept through its range. The digital display of the frequency counter is blanked as the system 500 is initially activated and remains blanketed until a dip is detected. As the dialysis cartridge is brought near enough to the probe coil 412 to become inductively coupled, that condition is reflected back into the probe circuit 501 of system 500. A dip can therefore be detected during each frequency sweep, which causes the frequency counter 504 display to update once per sweep.

As the pressure changes, the resonant frequency of the sensor also varies, and this change can be detected by the GDO 408 and the frequency counter 504. This count will vary slightly with distance between probe coil 412 and LC sensor circuit 403 due to the loading effect of the probe coil 412 on the resonant circuit of the sensor thereof. The most accurate measurement of the resonant frequency of a tune circuit can be produced when the coupling between the probe coil and the LC sensor circuit 403 is as "loose" as possible.

Figure 6:
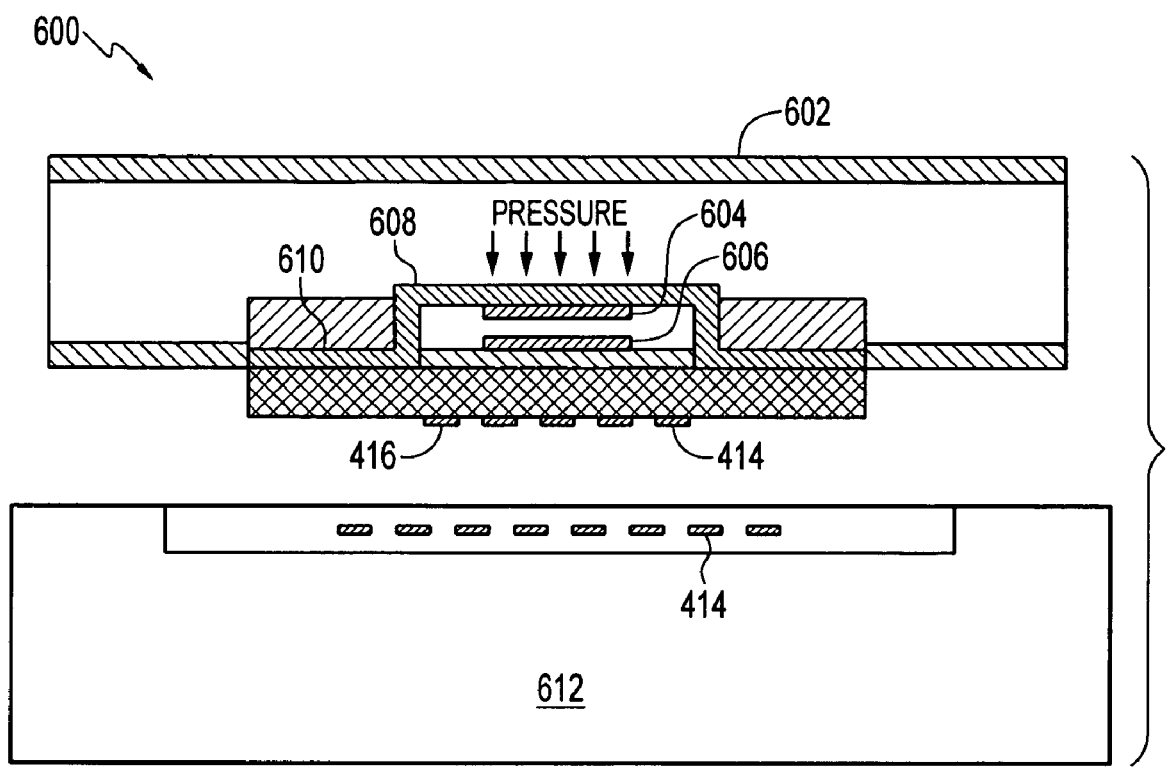
FIG. 6 illustrates a block diagram of a dialysis pressure sensor system, which can be implemented in accordance with an alternative embodiment.
Figure 7:
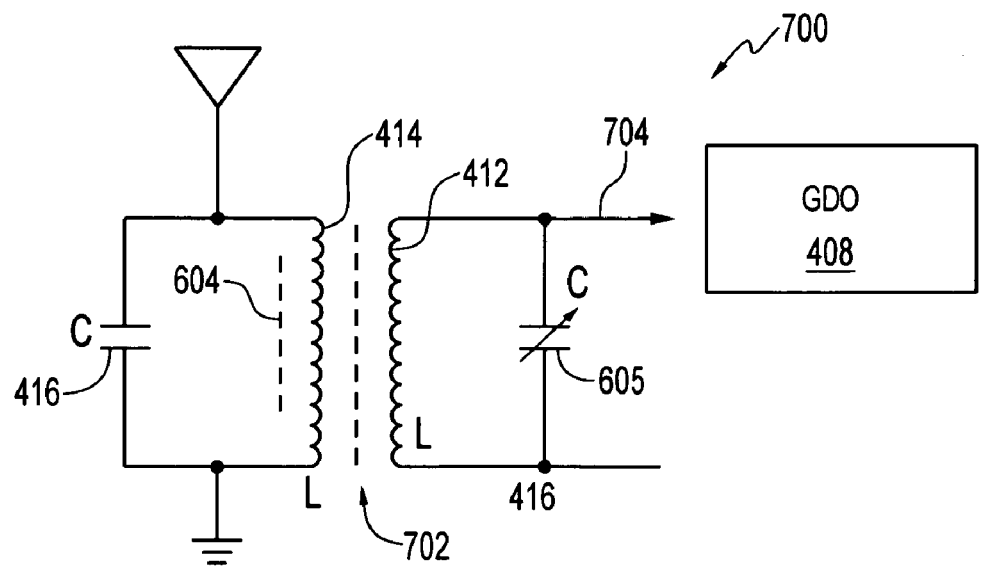
FIG. 7 illustrates a schematic diagram of a system, which represents electrically some of the operational functionality of system, in accordance with the alternative embodiment of FIG. 6.

FIG. 6 illustrates a block diagram of a dialysis pressure sensor system 600, which can be implemented in accordance with an alternative embodiment. FIG. 7 illustrates a schematic diagram of a system 700, which represents electrically some of the operational functionality of system 600, in accordance with the alternative embodiment of FIG. 6. Note that in FIGS. 1–7, identical or similar parts are generally indicated by identical reference numerals.

System 600 is generally composed of a dialysis machine 612 that includes an interrogation system coil 412, which is similar to coil 412 depicted in FIGS. 4–5. A disposable cassette cartridge 602 (or tube set) is associated with dialysis machine 612 and can be disposed above a sensor diaphragm 608, which in turn is located above a substrate 610. Note that sensor diaphragm 608 depicted in FIG. 6 is analogous to diaphragm 112 depicted in FIG. 1. Similarly, substrate 610 depicted in FIG. 6 is similar to substrate 101 depicted in FIG. 1.

A ferrite core 604, which is analogous to ferromagnetic materials 106 illustrated in FIG. 1, is located near a capacitor 606. A trim capacitor 416 (see capacitor 416 depicted in FIGS. 4–5) is disposed proximate to a sensor coil 414 (i.e., see coil 414 depicted in FIGS. 4–5). The foregoing components can be utilized to implement an inductively coupled pressure sensor configured from low cost materials (e.g., PCB and stamped diaphragm 608). Varying the inductance can be accomplished via the moveable iron core 604 and/or a capacitive pressure sensor that includes capacitor 606.

The inductance of the coil 414 increases directly as the permeability of the core material 604 increases or the capacitance associated with capacitor 606 changes. If a coil is wound around iron or ferrite core 604, the permeability of core 604 is high. If the iron or ferrite core 604 is pulled away from the coil of wire formed by coil 414, the permeability of the core 604 decreases. As the permeability of the core 604 decreases, the inductance of the coil 414 also decreases. Such a configuration increases the frequency of the resonating circuit. The permeability of the core 604 or inductance of the coil 414 changes with mechanical movement induced by pressure change.

Note that in FIG. 7, system 700, which is associated with system 600, indicates that calibration can be accomplished by the use of a trimmable capacitor 416 or an adjustable capacitor 605. The iron core 604 located on the pressure diaphragm 608 of FIG. 6 is also indicated in FIG. 7, disposed proximate to coil 414, which in turn is disposed opposite coil 412 thereby providing an inductively coupled spacing 702. Additionally, arrow 704 indicates that voltage output signals can be provided to Grid Dip Oscillator (GDO) 408. In general, a sensor/transponder circuit is composed of resonant LC circuit components 414 and 416. Such a resonant LC circuit of the sensor (e.g., see sensor 403) can be coupled electromagnetically to an external detection system (e.g., transmitter/receiver). The oscillator 408 can operate in a 5 to 500 MHz range and is frequency swept at an audio rate. Oscillator 408 can experience a power dip at the sensor's resonant frequency and the analyzer circuit 401 or 501 can be utilized to detect this dip. Interrogation distance is generally influenced by coupling coefficient, power, efficiency of antenna, size of coil and so forth.

Figure 8:
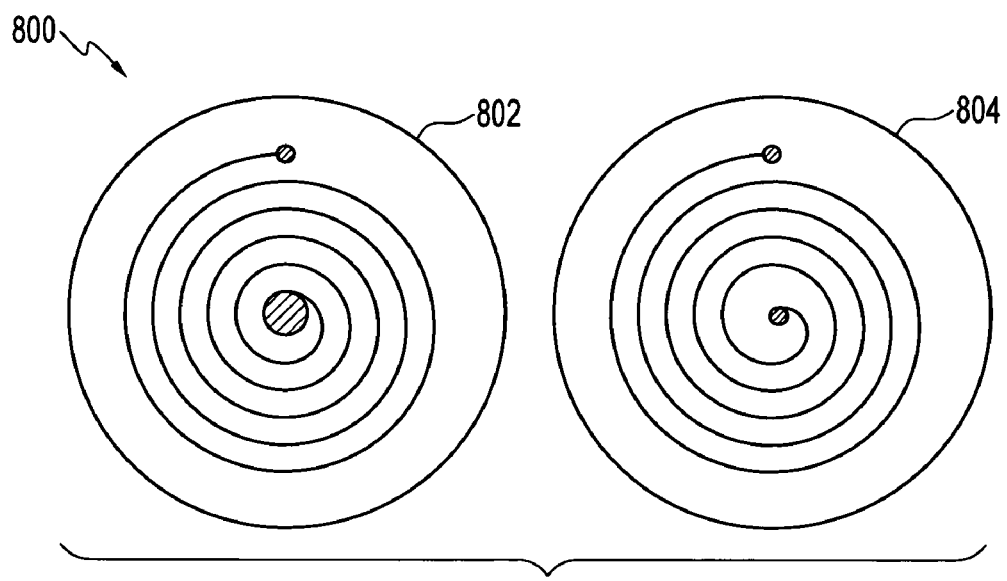
FIG. 8 illustrates a configuration of inductors, which can be implemented in accordance with an embodiment.
Figure 9:
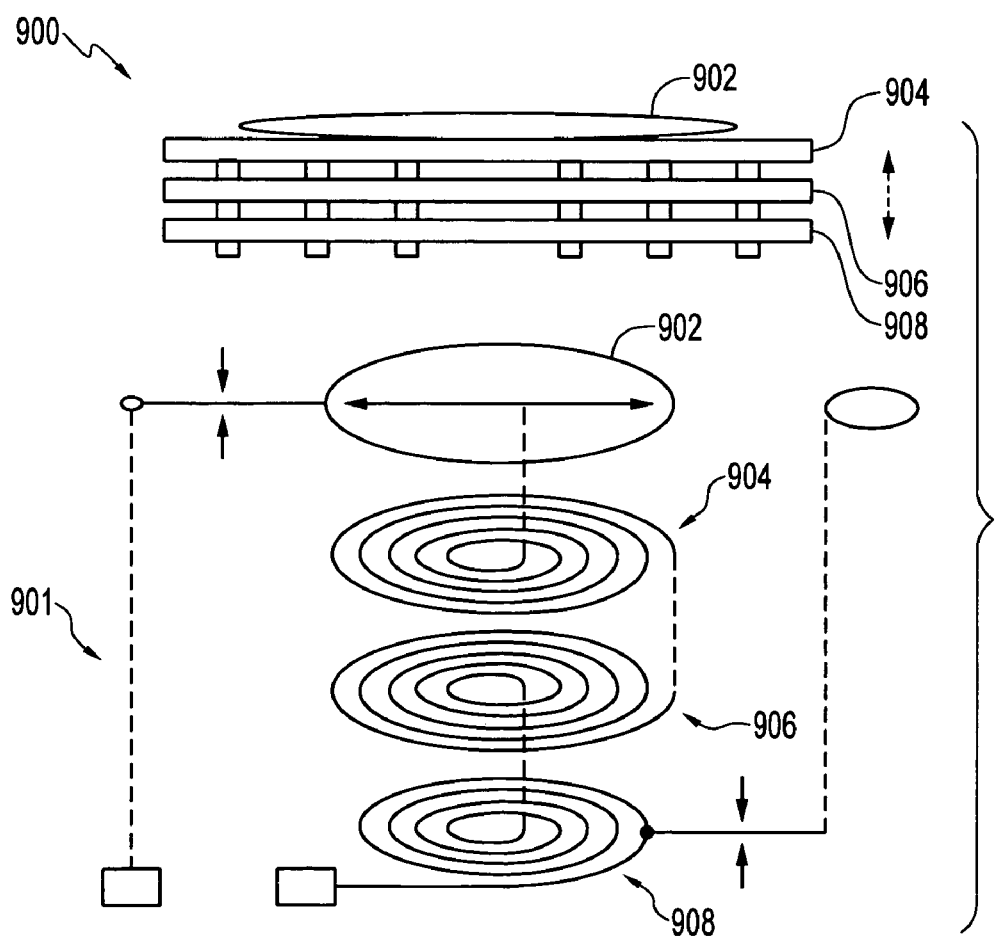
FIG. 9 illustrates a view of a multiple layer system of planar inductors, which can be implemented in accordance with an embodiment.

FIG. 8 illustrates a configuration of inductors 802 and 804, which can be implemented in accordance with an embodiment. Inductor 802 can be implemented, for example, as inductor or coil 412 depicted herein. Similarly, inductor 804 can be implemented, for example, as inductor or coil 414 described herein. FIG. 9 illustrates a view 901 of a multiple layer system 900 of planar inductors 904, 906, and 908, which can be implemented in accordance with an embodiment.

Figure 10:
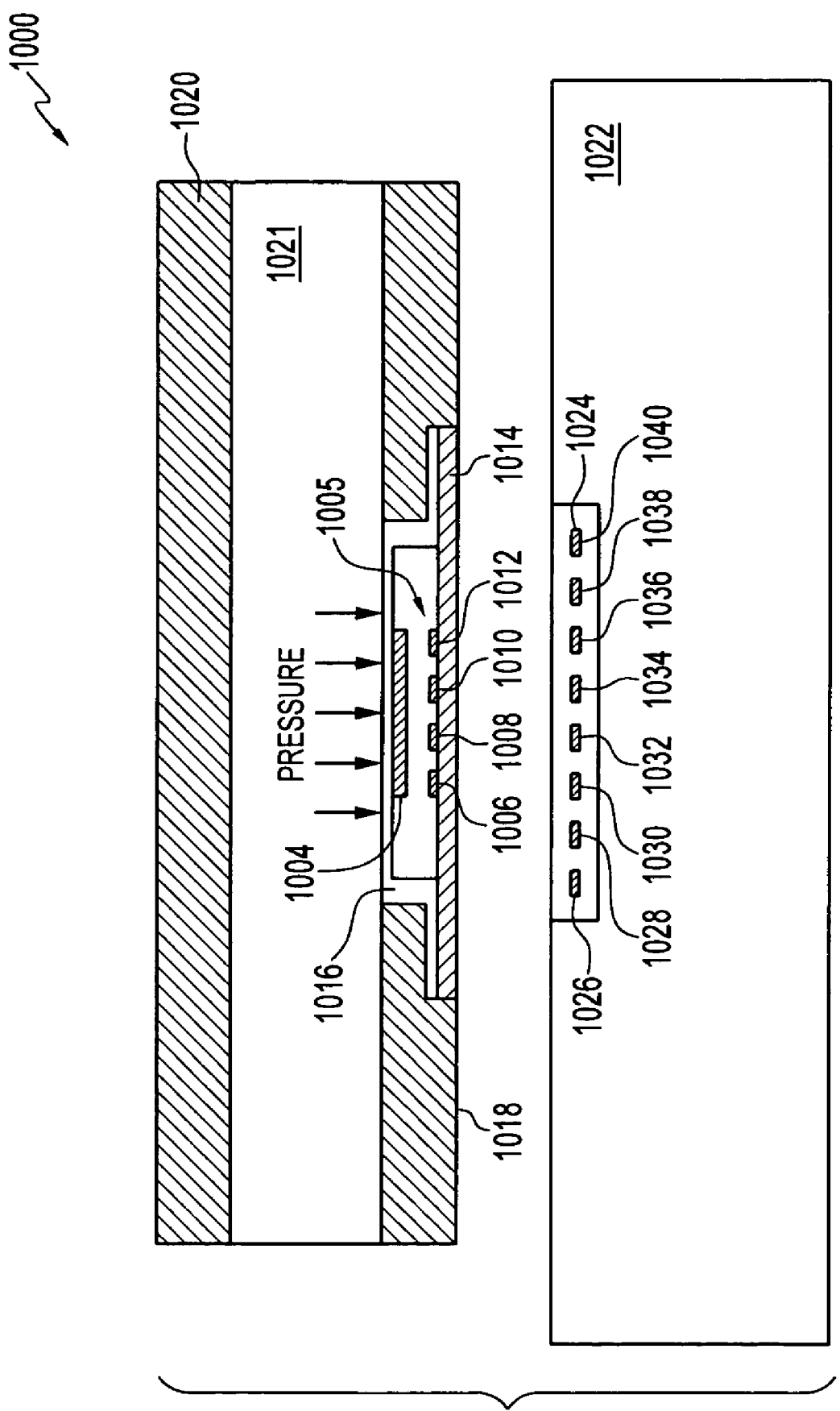
FIG. 10 illustrates a view of an inductively coupled LC sensor system, which may be implemented in accordance with a preferred embodiment.

FIG. 10 illustrates a view of an inductively coupled LC sensor system 1000, which may be implemented in accordance with a preferred embodiment. System 1000 and the configurations depicted in FIGS. 11–15 can be implemented in the context of an LC wireless sensor. There are three possible configurations for such configurations. First, the LC wireless sensor or system can be implemented with a variable inductor (L) and a variable capacitor (C). Second, the LC wireless sensor or system can be implemented with a variable C. Third, the LC wireless sensor or system can be implemented with a variable L. System 1000 generally includes, for example, a pressure diaphragm 1016 formed on a substrate 1014. A ferrite core 1004 is disposed proximate to a sensor coil 1005 composed of sensor coil portions 1006, 1008, 1010, 1012 and 1014. System 1000 also includes a disposable cassette cartridge or tube set 1021, which includes tube walls 1018 and 1020. The tube set 1021 and the sensor coil 1005 and substrate 1014 and associated components are disposed proximate to a medical apparatus 1022 such as, for example, a dialysis machine. The medical apparatus 1022 includes an interrogation system coil 1024 that is composed of coil portions 1026, 1028, 1030, 1032, 1034, 1036, 1038, and 1040. System 1000 can thus be utilized as an inductively coupled LC sensor.

In general, the movement of the pressure diaphragm 1016 can change with capacitance, inductance or both. The sensitivity of the design configurations depicted, for example, in FIGS. 10–15 is as follows: Variable L and C>Variable C>Variable L. In variable L and C design, a conductor and ferromagnetic plates such as ferrite core 1004 can be provided on the pressure diaphragm 1016 in order to change pressure, which also results in a change in L and C at the same time. System 1000 can be implemented as a wireless and/or wired pressure sensor, depending upon design considerations.

Figure 11:
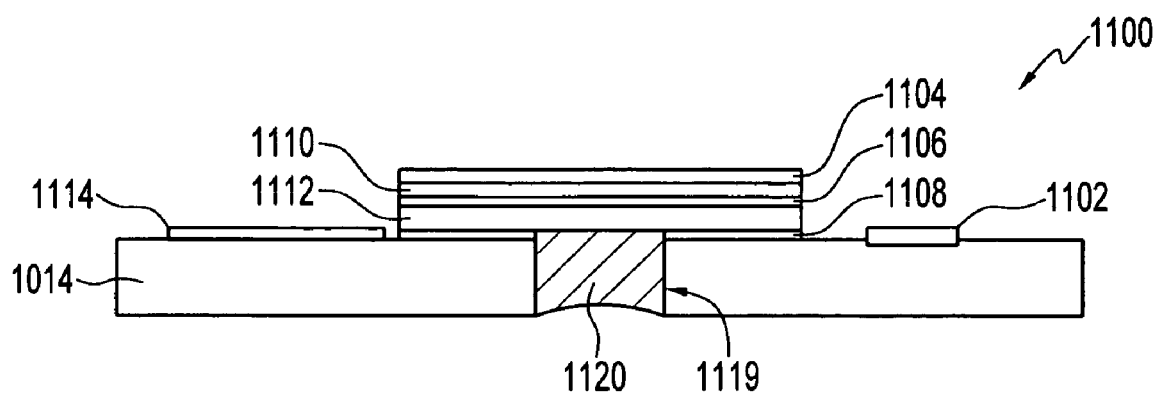
FIG. 11 illustrates a side view of a trimmable disposable PVDF pressure sensor system, which can be implemented in accordance with a preferred embodiment.

FIG. 11 illustrates a side view of a trimmable disposable PVDF pressure sensor system 1100, which can be implemented in accordance with a preferred embodiment. Note that as utilized herein, the acronym "PVDF" refers generally to polyvinylidene fluoride, which is a highly non-reactive and pure thermoplastic fluoropolymer. PVDF is a dense, high-purity plastic that is used in critical applications, such as semiconductor manufacturing.

System 1100 operates in a manner similar to that of system 1000, with some variations in its structure. FIG. 11 can include, for example, substrate 1014 upon which an antenna 1114 is located proximate to a first bonding layer 1108. A PVDF layer 1112 is disposed above the first bonding layer 1108. A second bonding layer 1106 is formed above the PVDF layer 1112. A copper IDT (Interdigital Transducer) layer 1110 can then be formed above the second bonding layer 1106. Finally, a protective cover layer 1104 may be formed above the IDT layer 1110. A trimmable or adjustable capacitor 1102 can also be disposed on substrate 1014 as indicated in FIG. 11. Note that a gel 1120 can also be disposed in a cavity 1119 formed from substrate 1014. Note that antenna 1114 can transmit signals via RF radiation, wherein such signals include data indicative of pressure. Additionally, a receiver such as that of receiver 305 can be utilized, which receives the signal transmitted wirelessly from antenna 1114.

Figure 12:
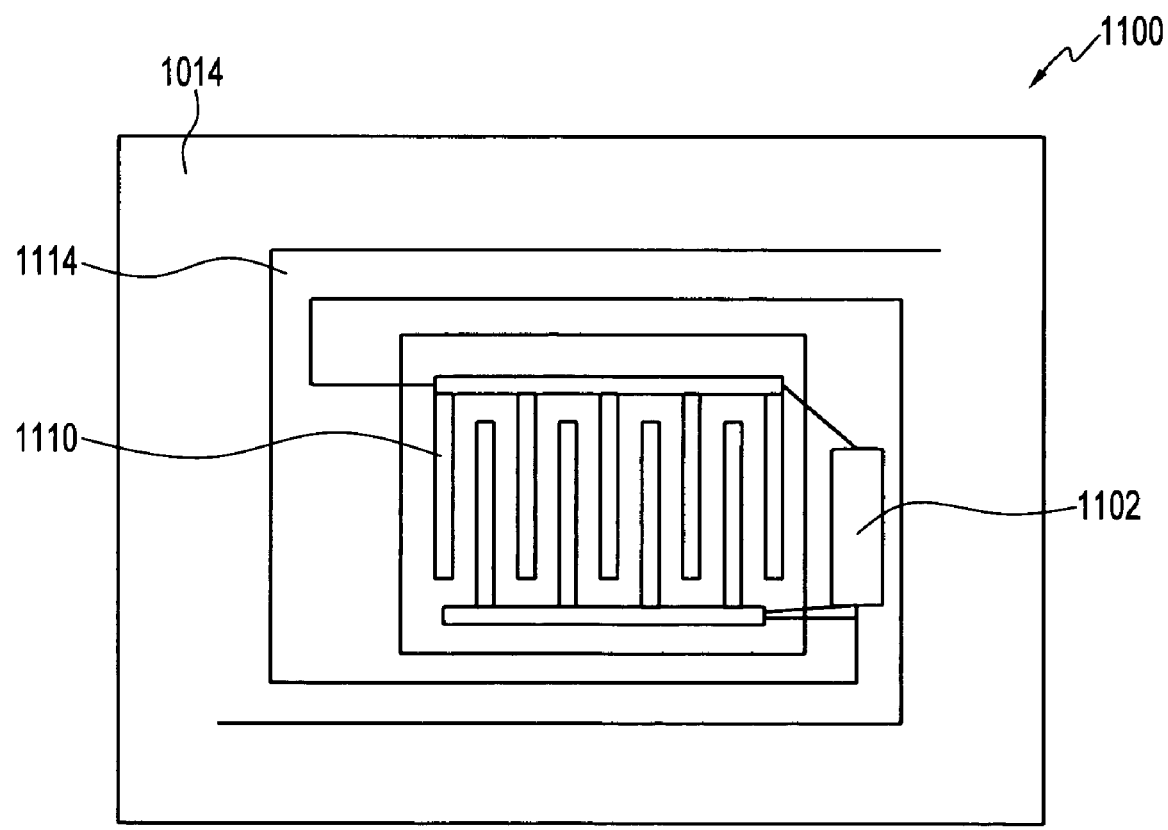
FIG. 12 illustrates a top view of a trimmable disposable PVDF pressure sensor system, which can be implemented in accordance with a preferred embodiment.

FIG. 12 illustrates a top view of the trimmable disposable PVDF pressure sensor system 1200 depicted in FIG. 11 in accordance with a preferred embodiment. Note that in FIGS. 11–12, identical or similar parts or elements are generally indicated by identical reference numerals. Note that the PVDF layer 1112 may have a thickness in a range of 50 μm to 120 μm depending upon design considerations. Additionally, the IDT period associated with the IDT 1110 may be for example, 0.4 mm with an example width of 0.2 mm for 10 IDT fingers. This, of course, represents only one possible embodiment. Numerous variations to such embodiments may be possible, depending upon design goals. Note that the IDT 1110 can be configured from a metal or a metal alloy. The IDT 1110 can be formed from a metal, such as one or more of the following: Cu, Al, Cr, Ag, Au, Pd, Ni, Cd, Zn, Mg, Fe, Sn, Pb, Ti, Ta, Sc, V, Mn, Co, W, Ir, or Pt. The choice of metal utilized for IDT 1110 depends largely on design considerations.

Figure 13:
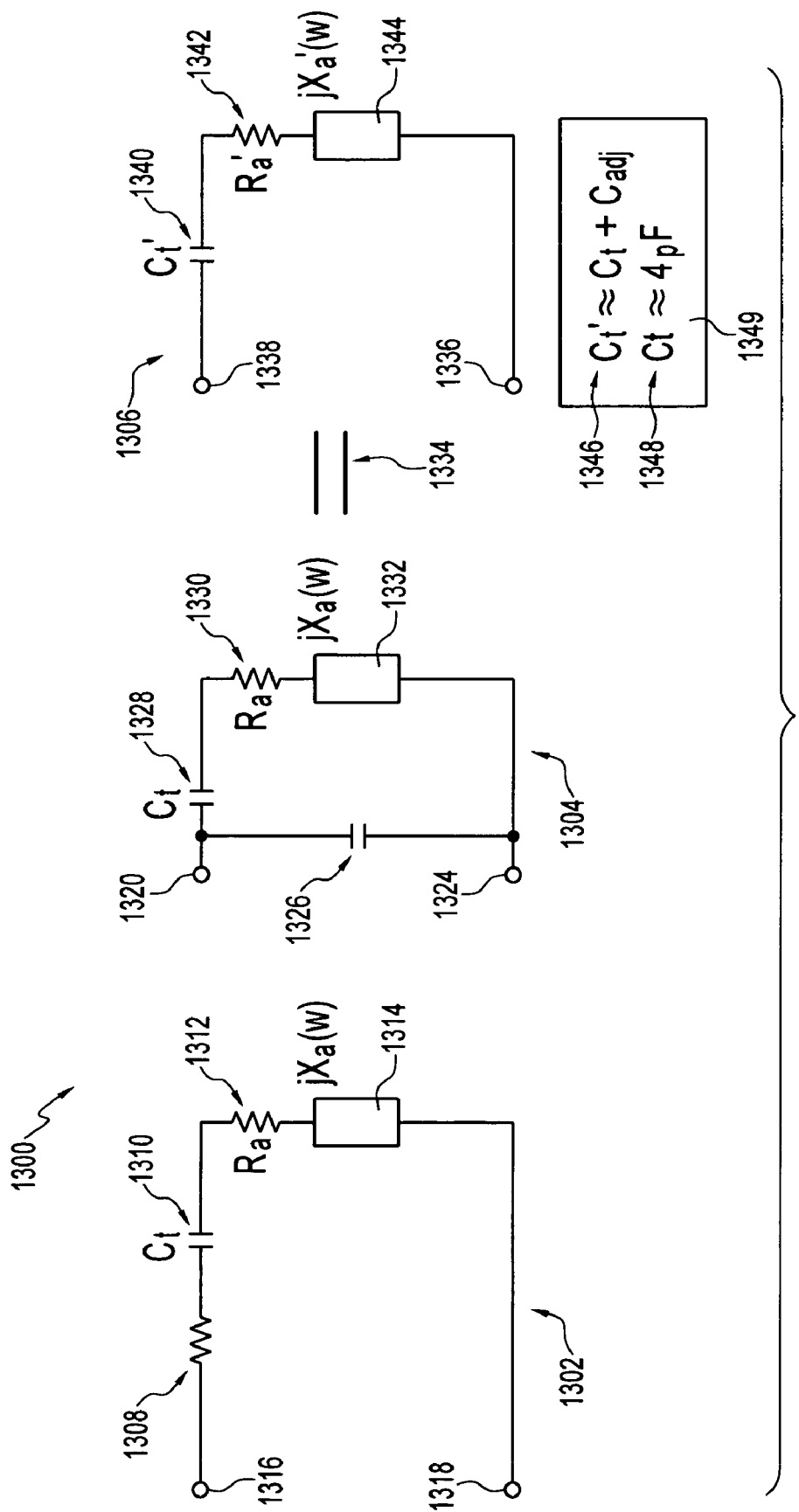
FIG. 13 illustrates a schematic diagram of an equivalent circuit configuration for an adjustable PVDF SAW sensor, which can be implemented in accordance with a preferred embodiment.

FIG. 13 illustrates a schematic diagram of an equivalent circuit configuration for an adjustable PVDF SAW sensor such as that depicted in FIGS. 10–12, in accordance with a preferred embodiment. As indicated in FIG. 13, a circuit 1302 is illustrated, which includes a resistor 1308 in series with a capacitor 1310 and a resistor 1312. A general circuit component 1314 is also depicted in series with resistor 1312. The general circuit component 1314 is depicted in FIG. 13 for equivalent circuit purposes. An adjustable capacitor circuit 1304 is also indicated in FIG. 13. Note that resistor 1308 is connected to a node 1316, while the general circuit component 1314 is connected in series to a node 1318.

The adjustable capacitor circuit 1304 includes a capacitor 1328 connected to an adjustable capacitor 1326 at a node 1320. The capacitor 1328 is also connected to a resistor 1330 which in turn is connected in series to a general circuit component 1332. The capacitor 1328, the resistor 1330 and the general circuit component 1332 are connected in parallel to the adjustable capacitor 1326. The capacitor 1326 is located between node 1320 and a node 1325.

The electrode resistance circuit 1302 and the adjustable capacitor 1304 are combined to form an electrical equivalent circuit 1306. Note that the "equal" sign 1334 depicted in FIG. 13 represents this equivalent functionality. In general, equivalent circuit 1306 includes a capacitor 1340 connected in series with a resistor 1342, which in turn is connected to a general circuit component 1344. Note that capacitor 1340 is connected to a node 1338, while the general circuit component 1344 is connected to a node 1336. A block 1349 generally includes equations 1346 and 1348, which are representative of the equivalent circuit 1306.

Figure 14:
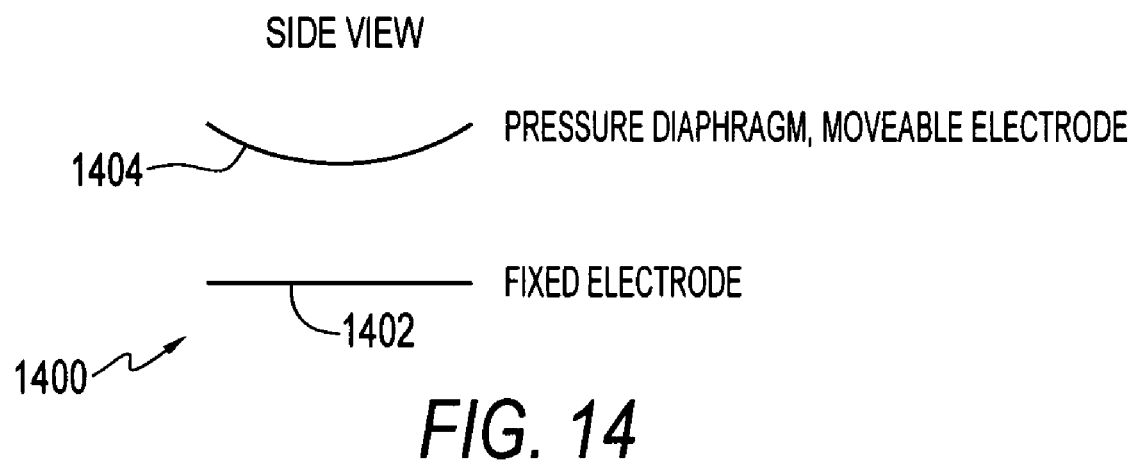
FIG. 14 illustrates a high-level schematic side view of a pressure diaphragm and moveable and fixed electrodes in accordance with a preferred embodiment.
Figure 15:
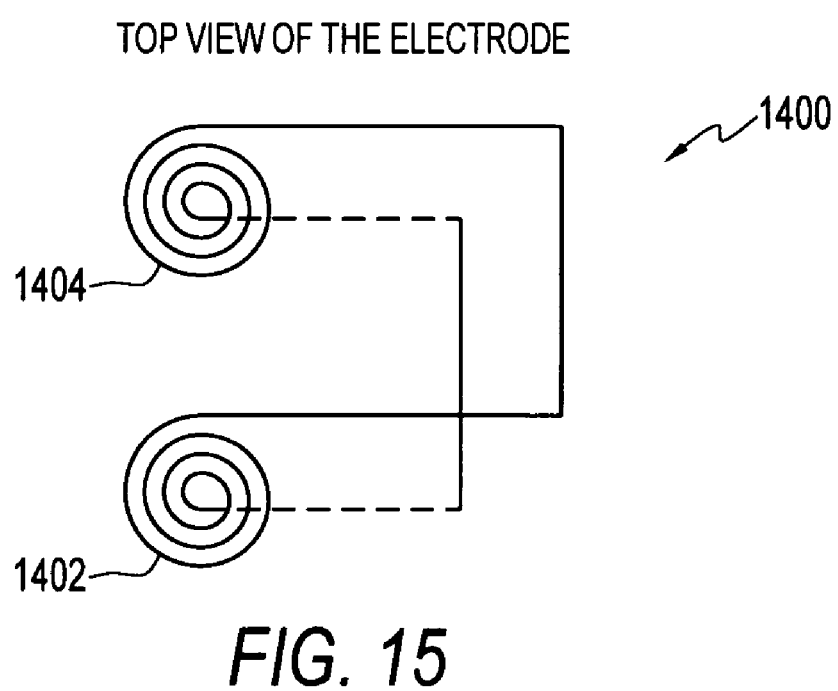
FIG. 15 illustrates a high-level schematic to view of the moveable and fixed electrodes depicted in FIG. 14 in accordance with a preferred embodiment.

FIG. 14 illustrates a high-level schematic side view of a system 1400 that includes a pressure diaphragm/moveable electrode 1404 and a fixed electrode 1402 in accordance with a preferred embodiment. FIG. 15 illustrates a high-level schematic to view of the system 1400 depicted in FIG. 14 in accordance with a preferred embodiment. Note that in FIGS. 14 and 15, identical or similar parts or elements are generally indicated by identical reference numerals.

What is claimed is:

1. A disposable pressure sensor, comprising:
   a substrate and a pressure diaphragm formed upon said substrate;
   a sensor antenna connected to a capacitor formed on said substrate and surrounded by said pressure diaphragm; and
   wherein said substrate is configured to include a gap in which a gel is located below a first bond layer and a PVDF layer formed thereon and wherein a second bond layer is formed above said PVDF layer followed by a layer of interdigital transducers, such that when said pressure diaphragm is exposed to a pressure, said diaphragm moves close to said PVDF layer or said capacitor, thereby resulting in an electric field change in said PVDF layer and at least one interdigital transducer among said layer of interdigital transducers to provide an indication of pressure.

2. The sensor of claim 1 wherein said capacitor comprises a variable capacitor.

3. The sensor of claim 1 wherein said capacitor is trimmed by a laser.

4. The sensor of claim 1 wherein said at least one interdigital transducer comprises a metal or a metal alloy.

5. The sensor of claim 4 wherein said metal comprises at least one of the following: Cu, Al, Cr, Ag, Au, Pd, Ni, Cd, Zn, Mg, Fe, Sn, Pb, Ti, Ta, Sc, V, Mn, Co, W, Ir, or Pt.

6. The sensor of claim 4 wherein said metal alloy comprises binary, ternary or quadruple phase diagrams of metal or non-metal elements.

7. The sensor of claim 1 wherein said sensor antenna transmits a signal through RF radiation, wherein said signal comprises said indication of pressure.

8. The sensor of claim 7 further comprising a receiver that receives said signal transmitted wirelessly from said sensor antenna.

9. The sensor of claim 8 wherein said receiver collects frequency and signal strength data that is indicative of said pressure.

10. The sensor of claim 9 wherein the said at least one interdigital transducer collects energy from a piezoelectric effect associated with said PVDF layer.

11. The sensor of claim 9 further comprising a medical apparatus disposed proximate to said substrate and said sensor coil, wherein said medical apparatus comprises an interrogation system coil.

12. The sensor of claim 11 wherein said disposable pressure sensor is connected to a disposable cartridge.

13. The sensor of claim 11 wherein said disposable pressure sensor is connected to a tube set.

14. A disposable pressure sensor, comprising:
   a substrate and a pressure diaphragm formed upon said substrate;
   a sensor antenna connected to a variable capacitor formed on said substrate and surrounded by said pressure diaphragm, wherein said variable capacitor is trimmed by a laser; and
   wherein said substrate is configured to include a gap in which a gel is located below a first bond layer and a PVDF layer formed thereon and wherein a second bond layer is formed above said PVDF layer followed by a layer of interdigital transducers, such that when said pressure diaphragm is exposed to a pressure, said diaphragm moves close to said PVDF layer or said variable capacitor, thereby resulting in an electric field change in said PVDF layer and at least one interdigital transducer among said layer of interdigital transducers to provide an indication of pressure, wherein said at least one interdigital transducer comprises a metal or a metal alloy.

15. The sensor of claim 14 wherein said metal comprises at least one of the following: Cu, Al, Cr, Ag, Au, Pd, Ni, Cd, Zn, Mg, Fe, Sn, Pb, Ti, Ta, Sc, V, Mn, Co, W, Ir, or Pt.

16. The sensor of claim 14 wherein said metal alloy comprises binary, ternary or quadruple phase diagrams of metal or non-metal elements.

17. A disposable pressure sensor, comprising:
   a substrate and a pressure diaphragm formed upon said substrate;
   a sensor antenna connected to a capacitor formed on said substrate and surrounded by said pressure diaphragm;
   a gap configured from said substrate, wherein a gel is located in said gap below a first bond layer and a PVDF layer formed thereon and wherein a second bond layer is formed above said PVDF layer followed by a layer of interdigital transducers, such that when said pressure diaphragm is exposed to a pressure, said diaphragm moves close to said PVDF layer or said capacitor, thereby resulting in an electric field change in said PVDF layer and at least one interdigital transducer among said layer of interdigital transducers to provide an indication of pressure; and
   wherein said at least one interdigital transducer comprises a metal or a metal alloy, wherein said metal alloy comprises binary, ternary or quadruple phase diagrams of metal or non-metal elements, and wherein the said at least one interdigital transducer collects energy from a piezoelectric effect associated with said PVDF layer.

18. The sensor of claim 17 wherein said sensor antenna transmits a signal through RF radiation, wherein said signal comprises said indication of pressure.

19. The sensor of claim 18 further comprising a receiver that receives said signal transmitted wirelessly from said sensor antenna.

20. The sensor of claim 19 wherein said receiver collects frequency and signal strength data that is indicative of said pressure.

* * * * *